US007109396B2

(12) United States Patent
Brunold et al.

(10) Patent No.: US 7,109,396 B2
(45) Date of Patent: Sep. 19, 2006

(54) METHOD FOR OBTAINING PLANTS ENRICHED IN CYSTEINE AND GLUTATHIONE CONTENT

(75) Inventors: Christian Brunold, Wabern (CH); Pascual Perez, Chanonat (FR)

(73) Assignee: Biogemma, Paris (FR)

( * ) Notice: Subject to any disclaimer, the term of this patent is extended or adjusted under 35 U.S.C. 154(b) by 584 days.

(21) Appl. No.: 10/169,667

(22) PCT Filed: Jan. 5, 2001

(86) PCT No.: PCT/FR01/00036

§ 371 (c)(1),
(2), (4) Date: Nov. 6, 2002

(87) PCT Pub. No.: WO01/49855

PCT Pub. Date: Jul. 12, 2001

(65) Prior Publication Data

US 2004/0123341 A1    Jun. 24, 2004

(30) Foreign Application Priority Data

Jan. 6, 2000    (FR) .................................. 00 00139

(51) Int. Cl.
*A01H 5/00*    (2006.01)
*C12N 15/82*    (2006.01)
*C12N 15/53*    (2006.01)

(52) U.S. Cl. ..................... 800/298; 800/278; 536/23.2; 435/320.1; 435/419

(58) Field of Classification Search ..................... None
See application file for complete search history.

(56) References Cited

U.S. PATENT DOCUMENTS 6,504,085 B1 *  1/2003  Howard ....................... 800/288
6,576,819 B1 *  6/2003  Leustek ....................... 800/320
6,730,827 B1 *  5/2004  Falco .......................... 800/295

FOREIGN PATENT DOCUMENTS

| JP | 06 038770 | 2/1994 |
| WO | WO 00/04161 | 1/2000 |
| WO | WO 00/49165 | 8/2000 |

OTHER PUBLICATIONS

Suter et al (2000, J. Biol. Chem. 275:930-936).*
R. Hell, "Molecular Physiology of Plant Sulfur Metabolism", Planta, Springer Verlag, DE, vol. 202, 1997, pp. 138-148.
A. Prior et al., "Structural and kinetic properties of adenylyl sulfate reductase from Catharanthus roseus cell cultures", Biochimica et Biophysica Acta, Amsterdam, NL, vol. 1430, 1999, pp. 25-38.
S. Heiss et al., "Cloning sulfur assimilation genes of *Brassica Juncea* L.: cadmium differentially affects the expression of a putative low-affinity sulfate transporter and isoforms of ATP sulfurylase and APS reductase", Plant Molecular Biology, Nijhoff Publishers Dordrecht, NL, vol. 39, Mar. 1999, pp. 847-857.
A. Seyta et al., "Sulfate Reduction in higher plants: molecular evidence for a novel 5'-adenylylsulfate reductase", Proceedings of the National Academy of Sciences of USA, National Academy of Science, Washington, US, vol. 93, Nov. 1996, pp. 13383-13388.
J.F. Gutierrez-Marcos et al., "Three members of a novel small gene-gamily from *Arabidopsis* able to complement functionally an *Escherichia coli* mutant defective in PAPS reductase activity encode proteins with a thioredoxin-like domain and "APS reductase activity", Proceedings of the National Academy of Sciences of USA, National Academy of Science, Washington, US, vol. 93, Nov. 1996, pp. 13377-13382.
M. Suter et al., "Adenosine 5'-Phosphosulfate Sulfotransferase and Adenosine 5'-Phosphosulfate Reductase Are Identical Enzymes", Journal of Biological Chemistry, American Society of Biological Chemists, Baltimore, MD, US, vol. 275, No. 2, Jan. 14, 2000, pp. 930-936.
J-A Bick et al, "Glutaredoxin function for the carboxyl-terminal domain of the plant-type 5'-adenylylsulfate reductase", Proceedings of the National Academy of Science, Washington, US, vol. 95, Jul. 1998, pp. 8404-8409.
U. Neuenschwander et al., "Regulation of Sulfate Assimilation by Light and O-Acetyl-L-Serine in Lemna minor L.", Plant Physiology, vol. 97, No. 1, 1991, pp. 253-258.
K. Saito, "Molecular Aspects of Sulfur Assimilation and Acclimation to Sulfur Supply in Plants", Stress Responses of Photosynthetic Organisms, NL, Elsevier Science, Amsterdam, 1998, pp. 215-226.
K. Saito et al., "Modulation of Cysteine Biosynthesis in Chloroplasts of Transgenic Tobacco Overexpressing Cysteine Synthase [O-Acetylserine(thiol)-lyase]", Plant Physiology, US, American Society of Plant Physiologists, Rockville, MD, No. 106, 1994, pp. 887-895.
C. Brunold et al., "Regulation of Sulfur Metabolism in Plants: First Molecular Approaches", vol. 58, 1997, pp. 164-186.
J-A Bick et al., "Plant sulfur metabolism—the reduction of sulfate to sulfite", vol. 1, No. 3, Jun. 1998, pp. 240-244.

* cited by examiner

Primary Examiner—Anne Kubelik
(74) Attorney, Agent, or Firm—Young & Thompson

(57) ABSTRACT

A method for obtaining a plant having an enriched content of cysteine and/or glutathione, including steps which consist in: transforming at least a plant cell with a vector containing an expression cassette including a sequence coding for an adenosine 5'-phosphosulphate reductase (APR); culturing the transformed cell so as to generate a plant containing in its genome the expression cassette.

18 Claims, 8 Drawing Sheets

METHOD FOR OBTAINING PLANTS ENRICHED IN CYSTEINE AND GLUTATHIONE CONTENT

The present invention relates to a method for obtaining plants enriched in cysteine and glutathione content, by transgenesis.

Higher plants use inorganic sulfate to satisfy their nutritional needs for sulfur. Sulfur is assimilated by plants by reduction of the sulfate to cysteine (Bick and Leustek, 1998). This amino acid is then involved in many functions in the plant (Rennenberg et al., 1990; Schmidt et al., 1992) and in particular participates in the synthesis of sulfur-containing proteins, such as membrane proteins.

The reduced sulfur is also found in methionine and several metabolites, such as glutathione, the biosynthetic pathway of which is linked to that of cysteine (Brunold et al., 1997).

Glutathione, which is a tripeptide (γ-glutamylcysteinylglycine), plays a role in the regulation of sulfur-containing nutrition, but also in the defense of plants against various stresses, such as drought cold, heat and detoxification of xenobionts such as heavy metals (Rennenberg et al., 1994; May et al., 1998).

The pathways for assimilating sulfate in plants are relatively complex and have not yet been completely elucidated. They involve a certain number of enzymes, including adenosine 5'-phosphosulfate reductase (APR).

The authors of the present invention have now developed a method for obtaining plants enriched in cysteine and/or glutathione content, by transgenesis and overexpression of a gene encoding an APR enzyme.

The invention is more particularly related to a method for obtaining a plant exhibiting an enriched cysteine and/or glutathione content, comprising the steps consisting in:
  transforming at least one plant cell with a vector containing an expression cassette comprising a sequence encoding an adenosine 5'-phosphosulfate reductase (APR);
  culturing the cell thus transformed so as to generate a plant containing said expression cassette in its genome.

The sequence encoding the APR may be a sequence which is heterologous with respect to said plant, or a sequence belonging to the same species, provided that it is expressed in amounts greater than the amount conventionally produced by a nontransformed plant.

Advantageously, said sequence encoding the APR is a sequence of the aquatic plant *Lemna minor* (water lentil), such as the attached sequence SEQ ID No. 1.

There are multiple advantages to using this Lemna enzyme: it in particular exhibits a high enzymatic activity (quantified at 40 μmol per minute per mg of protein) and is stable (up to 13 days at 0–4° C.).

It is, however, also possible to use nucleotide sequences encoding other APRs, such as, for example, that characterized in *Arabidopsis thaliana* (Gutierrez-Marcos et al., 1996) or in *Brassica juncea* (Heiss et al., 1999).

The nucleic acid encoding the APR is inserted into a nucleotide construct, called expression cassette, in which said coding sequence is functionally linked to elements which allow the expression thereof and, optionally, the regulation thereof.

Among these elements, mention may in particular, be made of transcription promoters, activators and terminators.

In general, use may be made, for example, of a strong promoter, such as the 35S promoter (Kay et al., 1987) or the rice actin promoter followed by the rice actin intron (RAP-RAI) contained in the plasmid pAct1-F4 (McElroy et al., 1991), or a tissue-specific promoter. Use may, in particular, be made of a promoter which allows expression of the sequence of the APR in the seeds of the plant obtained. By way of example, mention may be made of the wheat HMWG promoter, which allows expression in seeds.

Among the terminators which can be used in the constructs of the invention, mention may in particular be made of the 3' end of the nopaline synthase gene of *Agrobacterium tumefaciens*.

The expression cassette is inserted into a nucleotide vector, such as a plasmid, which may also comprise a marker gene, for example a gene for selecting a transformed plant from a plant which does not contain the foreign DNA transfected. As a marker gene, mention may in particular be made of a gene which confers resistance to an antibiotic (Herrera-Estrella et al., EMBO J. 2, 987–995 (1983)) or resistance to a herbicide (EP 242 246).

The vector thus constructed can be used to transform host cells, according to techniques known to those skilled in the art.

Mention may in particular be made of the methods of direct transfer of genes into plant cells, such as direct microinjection into plant embryoids (Neuhaus et al., 1987), infiltration under vacuum (Bechtold et al., 1993) or electroporation (Chupeau et al., 1989), or alternatively direct precipitation using PEG (Schocher et al., 1986) or bombarding particles covered with the plasmid DNA of interest, using a gun (M. Fromm et al., 1990).

According to another embodiment of the method of the invention, the plant cells are transformed with a vector as defined above, transferred into a cellular host capable of infecting said plant cells while allowing the integration, into the genome of the latter, of the nucleotide sequences of interest initially contained in the abovementioned vector genome. Advantageously, the cellular host used is a bacterial strain, such as *Agrobacterium tumefaciens*, in particular according to the method described in the article by An et al., (1986), or *Agrobacterium rhizogenes*, in particular according to the method described in the article by Guerche et al., (1987).

For example, the plant cells may be transformed by transferring the T region of the tumor-inducing extrachromosomal circular plasmid Ti of *Agrobacterium tumefaciens*, using a binary system (Watson et al., 1994). To do this, two vectors are constructed. In one of these vectors, the T region has been removed by deletion, with the exception of the right and left borders, a marker gene being inserted between them to allow selection in the plant cells. The other partner in the binary system is an auxiliary Ti plasmid, which is a modified plasmid which no longer has a T region but still contains the virulence genes vir required for transformation of the plant cell.

According to a preferred mode, the method described by Ishida et al., (1996) may be used to transform monocotyledons.

According to another protocol, the transformation is carried out according to the method described by Finer et al., (1992) using a particle gun with tungsten or gold particles.

A subject of the invention is also a plant or part of a plant, in particular seed, grain, fruit, leaf or tuber, which can be obtained using the method described above.

They may be large-scale crop plants (maize, wheat, rapeseed, sunflower, pea, soya, barley, etc.) or vegetables and flowers. Preferentially, plants may be chosen which are known to contain large protein stores, in particular cereal plants or leguminous plants such as the potato.

The hybrid transgenic plants, obtained by crossing at least one plant according to the invention, are also part of the invention.

In accordance with the present invention, a nucleic acid encoding an adenosine 5'-phosphosulfate reductase (APR) is used to obtain a transgenic plant exhibiting an enriched cysteine and/or glutathione content compared with a non-transformed plant.

It has thus been possible to obtain transgenic plants producing twice as much cysteine and twice as much glutathione than nontransformed plants using the method of the invention.

The plants with an enriched glutathione content in particular have the advantage of being more resistant to low temperatures. The cold-resistance of a nonresistant genotype at a temperature of 12° C. is increased by 30% when the glutathione is increased by 50%.

An increase in the cysteine content of a plant or part of a plant makes the latter particularly advantageous for preparing derived products, in particular food products, preferably for animal feed. The products which contain a transgenic plant or part of a plant enriched in cysteine and/or glutathione are also, moreover, part of the invention.

Advantageously, the plant cells may be cotransformed with a nucleic acid encoding a serine acetyltransferase (SAT), this being an enzyme involved in cysteine metabolism (Murillo et al., 1995; Saito et al., 1995 and Roberts et al., 1996), carried by the same vector as that carrying the sequence of the APR or by a different vector.

A combined overexpression of APR and of SAT makes it possible to obtain an increased augmentation of glutathione and cysteine.

The following figures and examples illustrate the invention without limiting the scope thereof.

LEGEND TO THE FIGURES

EXAMPLES

Example 1

Figure 1:
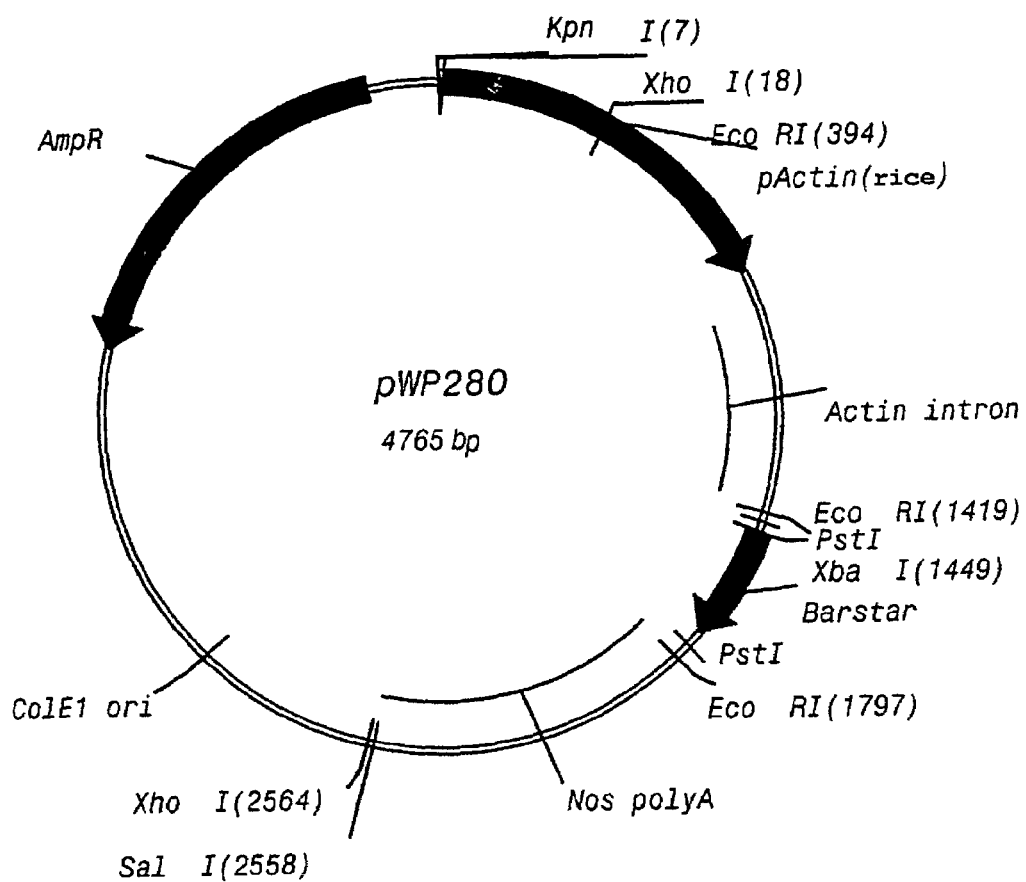
FIG. 1 represents a restriction map for the vector pWP280.

Construction of a Vector Containing the cDNA of the APR of *Lemna minor*

1. Production of the cDNA Sequence of the APR of *Lemna minor* a) Purification of the APR 40 g of *Lemna minor* plants are homogenized in the presence of 5'AMP. The homogenate is centrifuged and the supernatant is treated with $(NH_4)_2SO_4$ (ammonium sulfate) up to a concentration of 30%. The proteins precipitated are collected by centrifugation and dissolved in a buffer containing 5'AMP. The solution is passed over a chromatography column containing Sephacryl S-300HR. The fractions exhibiting an enzymatic activity of 50% or more of the more active fraction are subjected to chromatographic fractionation on Mono Q HR, Phenyl-Superose and Superose 12 HR. The most active fractions eluted from the last chromatographic column are concentrated to a volume of 50 μl and loaded onto a polyacrylamide gel under native conditions. After electrophoresis, the gel is cut into 2-mm segments. The segments are eluted and the eluates are analyzed with regard to the enzymatic activity of the APR. The eluates containing the greatest enzymatic activity are subjected to separation by SDS-PAGE. The gels are stained and the proteins are subjected to amino acid sequencing.

b) Isolation of the cDNA of the APR:

The central region of the APR was obtained from the *L. minor* RNA by RT-PCR using the sequence of the domains conserved between the APS reductase of *A. thaliana* and the PAPS reductases of bacteria and yeast, and the thioredoxin motif, to synthesize the oligonucleotide primers. The 750-base pair amplified fragment was completely sequenced on both its strands. Primers specific for the gene were synthesized for a 5'- and 3'-RACE using this sequence information. For the 5'-RACE, the first cDNA strand was synthesized from 0.5 μg of poly(A) RNA using a primer specific for the gene, SP1 (5'-ACTGGTCCTTGCGCTGGCCG-3' (SEQ ID No. 3)), the Moloney murine leukemia virus reverse transcriptase and a mixture of deoxynucleotides. The mRNA-cDNA hybrid was then purified from the nonincorporated primers and the nucleotides using the "GlassMax DNA Isolation Matrix System" (Life Technologies Inc.). For the linker, 10 pmol of oligo d(T) anchoring primers (AP, 5'-GACCACGCGTATCGATGTCGACT$_{16}$-3' (SEQ ID No. 4)) and of reverse anchoring primers (APrev, 5'-GTCGA-CATCGATACGCGTGGTC-3' (SEQ ID No. 5)) were hybridized. Then, the blunt ends of the linker were ligated to the RNA-cDNA hybrid at 15° C. overnight using 400 units of T4 ligase (BioLabs).

The following PCR amplification was carried out with the APrev primer and the nested primer SP2 (5'-GTGATCCAG-GCTCTGAGGCC-3' (SEQ ID NO. 6)). The PCR products were then separated on an agarose gel. For the second PCR amplification, the APrev primers and the third nested primer SP3 (5'-TCTGAGAGCTCTTCTAAGGGGC-3' (SEQ ID NO. 7)) were used. The major band (of approximately 640 base pairs) on the agarose gel was used as matrix. The PCR product was separated on an agarose gel and isolated using the "GlassMax DNA Isolation Matrix System" (Life Technologies Inc.). The DNA was cloned into a vector pCR 2.1 using the TA original cloning kit (Invitrogen) according to the manufacturer's instructions.

For the 3'-RACE, the first cDNA strand was synthesized from 0.5 µg of poly(A) RNA using the oligo d(T) anchoring primer, the A-MLV reverse transcriptase and the mixture of deoxynucleotides. The first PCR amplification was then carried out directly without any further purification step, using the AP and the primer specific for the gene, SP4 (5'-ACCAGGACAGCACGAGAGGG-3' (SEQ ID NO. 8)). The PCR product was separated by electrophoresis on an agarose gel.

For the second PCR amplification, the band on the agarose gel was used as matrix with the nested primer SP5 (5'-AAGGTGGTGGTGGGAGGACG-3'(SEQ ID NO. 9)) and the AP. After separation of the PCR products on an agarose gel, the major band (approximately 560 base pairs) was purified using the "GlassMax DNA Isolation Matrix System" (Life Technologies Inc.). The DNA was cloned into a vector pCR 2.1 using the TA original cloning kit (Invitrogen) according to the manufacturer's instructions.

The cDNA of the Lemna APR contains 1377 base pairs (SEQ ID NO. 1) and has an open reading frame (ORF) encoding a 459-amino acid protein (SEQ ID NO. 2). The deduced amino acid sequence contains a region of 30 residues from Ser-69 to Glu-98 which is identical to the sequence determined by N-terminal sequencing of the purified enzyme (Example 1a above).

2. Preparation of the Expression Cassettes

The standard cloning techniques which may be used for preparing the constructs are described in J. Sambrook et al., Molecular cloning, A laboratory manual, Second edition, Cold Spring Harbor Laboratory Press, 1989.

a) APR~35S for the Transformation of *Arabidopsis thaliana*

The Lemna APR was cloned, by RT-PCR (Sambrook et al., 1989), from total RNA isolated from whole Lemna plants. The 5' primer used CGTCTAGAGGCCATGGCG-GCCGCAGCAGCAACTATGGCG (SEQ ID NO. 10), generated an XbaI/NcoI site (the NcoI site being created at the level of the ATG initiation codon). The 3' AAAGAATTC-CACTCTAGAAGCGAAGAGAAGAGGC (SEQ ID NO. 11) specific for the 3' untranslated region of the Lemna APR generated, itself, an EcoRI/XbaI site. The isolated cDNA sequence of the Lemna APR contains a 1380-base pair open reading frame comprising a putative chloroplast transit peptide.

This amplified cDNA was then cloned into a vector pBluescript SK (Stratagene), at the Xba1 restriction sites. This clone, containing the open reading frame of the Lemna APR, was confirmed by sequencing.

The strategy for cloning the construct 35S promoter~APR~terminator is based on the use of the vector pRTL2-GUS/NiaDBamHI (Carrington et al., 1991, The plant cell, 3, 953–962). This vector contains the double 35S promoter, the untranslated TEV sequence (Carrington and Freed, 1990, Journal Virol., 64, 1590–1597), the GUS gene, a nuclear target sequence (Nia) and the 35S polyA signal. The GUS/Nia sequence of this vector was replaced with the Lemna APR sequence by cleaving the NcoI and XbaI restriction sites and ligating in the presence of T4 DNA ligase.

The construct thus generated was then subcloned into the binary vector pMON505 (Rogers et al., 1987, Methods in enzymology, 153, 253–277) using the HindIII site of the multiple cloning site of pMON505 and the HindIII sites of the 5' and 3' ends of said construct. This binary vector is used to transform the *Agrobacterium tumefaciens* strain GV3101 (Koncz and Schell, 1986, Mol. Gen. Genet., 204, 383–396), intended for the transformation of *Arabidopsis thaliana* subsequently described.

b) APR Actin Promoter (pPS103) for the Transformation of Maize

The cloning of the construct actin promoter~APR~Nos 3' uses, as basic plasmid, the plasmid pWP280 containing the cassette pActin-intron-Barstar-Nos polyA (FIG. 1), in which the Barstar fragment is replaced with the APR fragment.

The basic plasmid was obtained according to the following steps: the barstar gene (Hartley, 1988, J. Mol. Biol., 202, 913–915) was transferred, as an XbaI/HincII fragment, into an XbaI/SmaI site of the plasmid pW90, derived from the plasmid pJIT30 described by Guérineau et al., 1990, (Plant Mol. Biol., 15: 127–136) (CaMV 35S promoter replaced with the double 35S promoter and the polylinker region between the XbaI and EcoRI sites replaced with the SpeI, BamHI, SmaI and PstI sites). The CaMV polyA region of the plasmid obtained is replaced with the polyA region of pED23 (Dale et al., 1990, Gene, 91: 79–85), forming the plasmid pWP266. The CaMV double 35S promoter region is, finally, replaced with the rice actin promoter and the intron derived from pCOR113 (McElroy et al., 1991, Mol. Gen. Genet., 231: 150–160), forming the plasmid pWP280.

Figure 2:
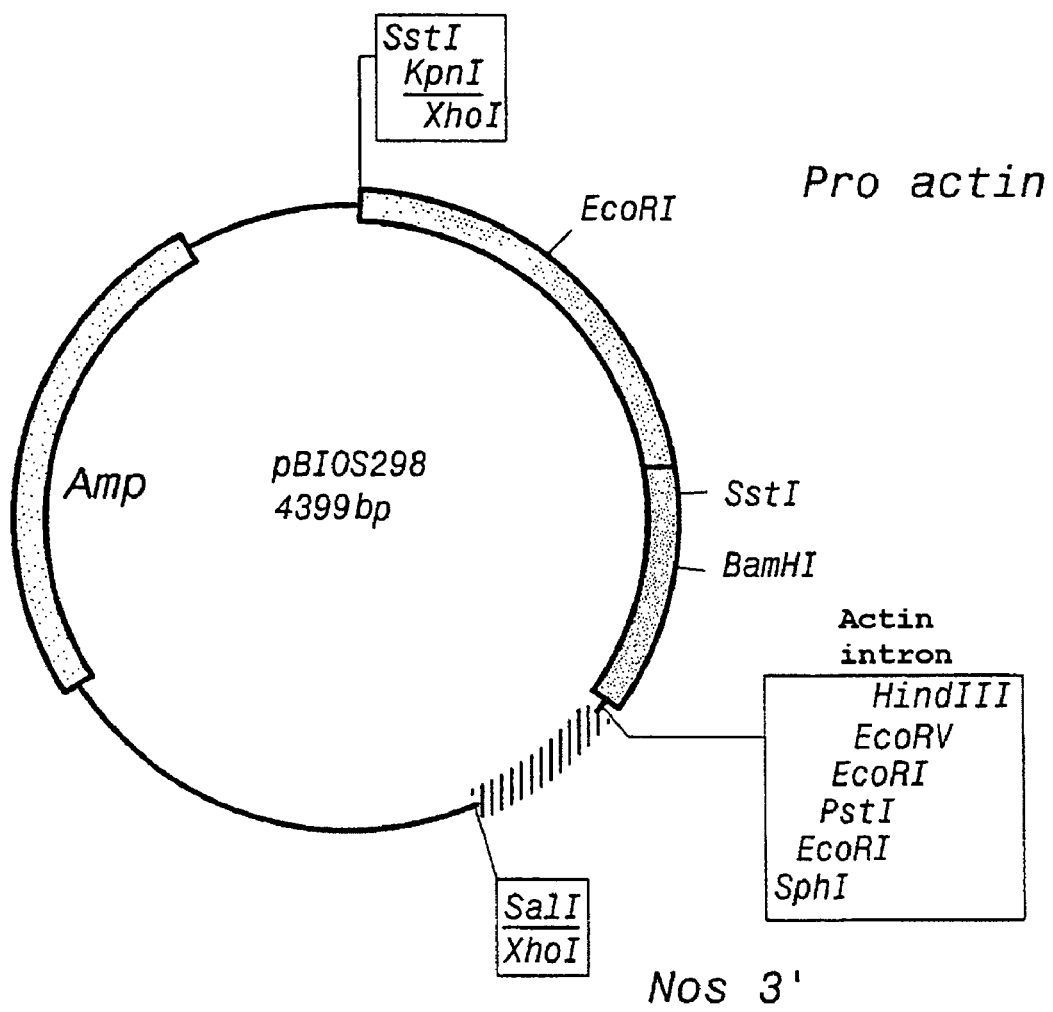
FIG. 2 represents a restriction map for the vector pBIOS298.
Figure 3:
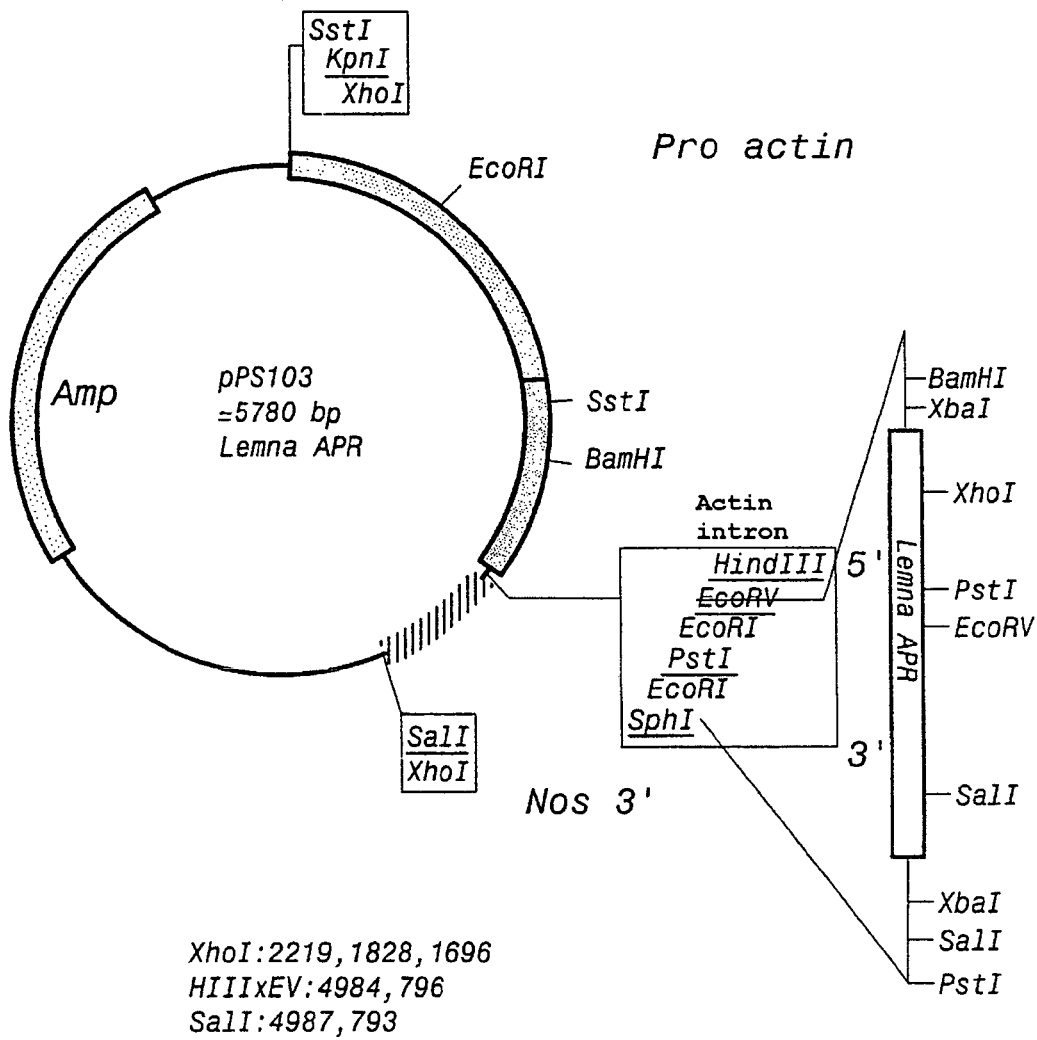
FIG. 3 represents a restriction map for the plasmid pPS103, containing a *Lemna minor* APR sequence associated with a rice actin promoter.

This plasmid pWP280 was then deleted of its barstar fragment by digestion with the PstI enzyme, and then religated on itself so as to give the vector pBIOS298 containing the fragment actin promoter-intron-multiple cloning site~Nos3' terminator (FIG. 2). This is then cleaved at the EcoRV and SphI sites of the multiple cloning site, so as to insert therein the fragment containing the cDNA sequence of the Lemna APR (1380 pb), obtained in parallel by digestion of the vector pPS101 (derived from the vector pUCAP described by F. A. van Engelen et al., 1995, Transgenic Research, 4, 288–290, by insertion of the APR sequence at the multiple cloning site) with the SmaI and SphI enzymes. The vector and the insert are mixed together with T4 DNA ligase for the step comprising ligation at the SphI and EcoRV sites (the SmaI and EcoRV cleavages having generated blunt-ended ends), producing the vector pPS103 (FIG. 3).

c) APR HMWG Promoter (pPS106) for the Transformation of Maize

The vector pBL 3214 is derived from a plasmid pBluescript II SK+ (Stratagene) into which the wheat HMWG (High Molecular Weight Glutenin) promoter sequence (Robert et al., 1989, Plant Cell, 1: 569–578), specific for the albumen of seeds, and an *Agrobacterium tumefaciens* Nos 3' terminator sequence (Depicker et al., 1982, Mol. Appl. Genet. 1: 561–573) has been inserted through the choice of specific restriction enzymes within the scope of those skilled in the art.

Figure 4:
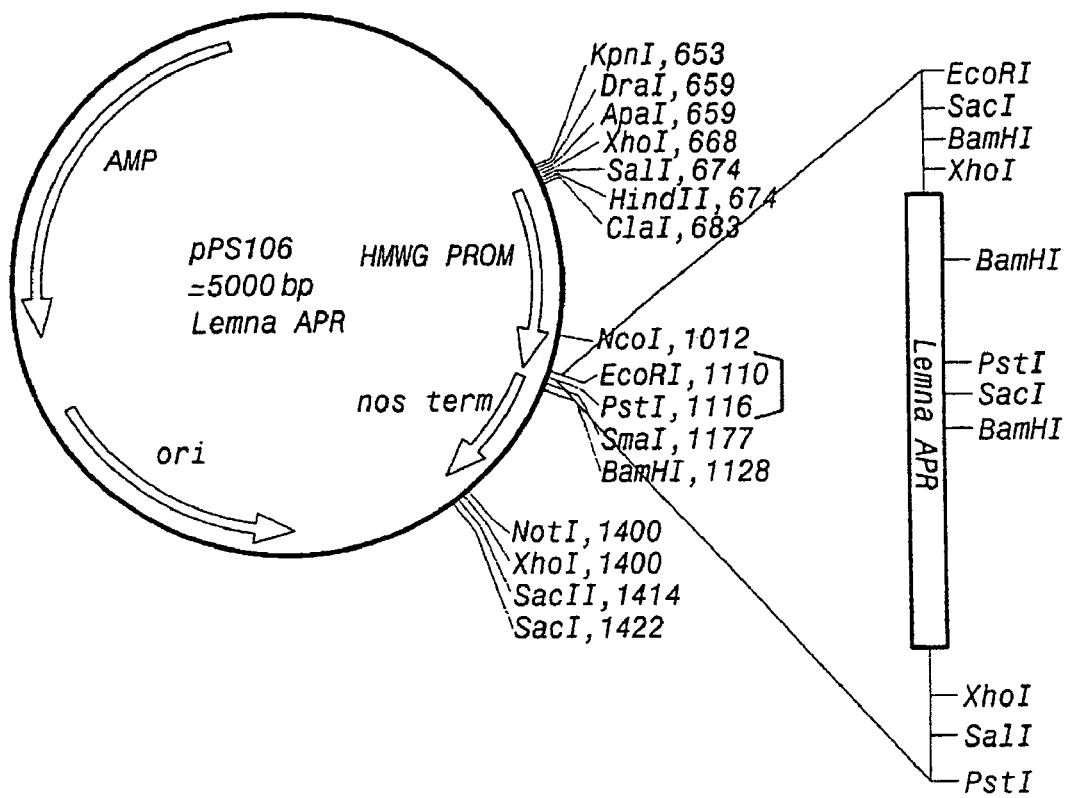
FIG. 4 represents a restriction map for the vector pPS106, containing a *Lemna minor* APR sequence associated with an HMWG promoter.

This vector is cleaved at the EcoRI and PstI sites of the multiple cloning site, in order to insert therein the fragment containing the cDNA of the Lemna APR, obtained in parallel from the vector pPS101 digested with the same EcoRI and PstI enzymes. The vector and the insert are ligated in the presence of T4 DNA ligase, so as to obtain the vector pPS106 (FIG. 4).

Example 2

Transformation of Plants

1. Transformation of Maize a) Particle Gun

The method used is based on the use of a particle gun identical to that described by J. Finer (1992). The target cells are rapidly dividing undifferentiated cells which have conserved an ability to regenerate whole plants. This type of cell makes up the embryogenic callus (termed type II) of maize. These calluses are obtained from immature embryos of the genotype HiII according to the method and on the media described by Armstrong (Maize Handbook; 1994, M. Freeling, V. Walbot Eds; pp. 665–671). Four hours before bombardment, these callus fragments, with a surface area of 10 to 20 mm$^2$, were placed at the center of a Petri dish containing a culture medium identical to the initiation medium, supplemented with 0.2 M of mannitol+0.2 M of sorbitol, in a proportion of 16 fragments per dish. The plasmids described in the preceding examples and carrying the APR sequences to be introduced are purified on a Qiagen® column according to the manufacturer's instructions. They are then precipitated on particles of tungsten (M10) according to the protocol described by Klein (1987). The particles thus coated are projected onto the target cells using the gun and according to the protocol described by J. Finer (1992). The dishes of calluses thus bombarded are then sealed using Scellofrais® and then cultured in the dark at 27° C. The first subculturing takes place 24 h later, and then every two weeks for 3 months on a medium identical to the initiation medium, supplemented with a selective agent. After 3 months, or sometimes earlier, calluses are obtained, the growth of which is not inhibited by the selective agent and which are usually and mainly composed of cells resulting from the division of a cell having integrated, into its genetic inheritance, one or more copies of the selection gene. The frequency of production of such calluses is approximately 0.8 callus per dish bombarded.

These calluses are identified, separated, amplified and then cultured so as to regenerate plantlets, modifying the hormonal and osmotic balance of the cells according to the method described by Vain et al. (1989). These plants are then acclimatized in a greenhouse where they may be crossed so as to produce hybrids or self-pollinated.

b) Transformation with *Agrobacterium*

Another transformation technique which can be used in the context of the invention uses *Agrobacterium tumefaciens*, according to the protocol described by Ishida et al. (1996), in particular on immature embryos taken 10 days after pollination. All the media used are referenced in the reference cited. The transformation begins with a coculturing phase in which the immature embryos of the maize plants are brought into contact with *Agrobacterium tumefaciens* LBA 4404 containing the superbinary vectors, for at least 5 minutes. The superbinary plasmid is the result of homologous recombination between an intermediate vector carrying the T-DNA containing the gene of interest and/or the selectable marker derived from the plasmids described in the preceding examples, and the Japan Tobacco vector pSB1 (EP 672 752) which contains: the virB and virG genes of the plasmid pTiBo542 present in the supervirulent *Agrobacterium tumefaciens* strain A281 (ATCC 37349) and a homologous region found in the intermediate vector allowing this homologous recombination. The embryos are then placed on LSAs medium for 3 days in the dark at 25° C. A first selection is carried out on the transformed calluses: the embryogenic calluses are transferred onto LSD5 medium containing phosphinotricine at 5 mg/l and cefotaxim at 250 mg/l (elimination or limitation of the contamination with *Agrobacterium tumefaciens*). This step is carried out for 2 weeks in the dark and at 25° C. The second selection step is carried out by transferring the embryos which have developed on LSD5 medium, onto LSD10 medium (phosphinotricine at 10 mg/l) in the presence of cefotaxim, for 3 weeks under the same conditions as above. The third selection step consists in excising the type I calluses (fragments of 1 to 2 mm) and in transferring them onto LSD10 medium, in the presence of cefotaxim, for 3 weeks in the dark at 25° C.

The plantlets are regenerated by excising the type I calluses which have proliferated and transferring them onto LSZ medium in the presence of phosphinotricine at 5 mg/l and cefotaxim for 2 weeks at 22° C. and under continuous light.

The plantlets which have regenerated are transferred onto RM+G2 medium containing 100 mg/l of augmentin for 2 weeks at 22° C. and under continuous illumination for the development step. The plants obtained are then transferred to a phytotron for the purpose of acclimatizing them.

2. Transformation of *Arabidopsis*

*Arabidopsis thaliana* can be easily transformed with a vector described in example 1, according to the method described in Bechtold et al., 1993, based on the infiltration, under vacuum, of *Arabidopsis* plants with an *Agrobacterium* strain containing a binary vector.

According to this method, *Agrobacterium* strains carrying a system of binary vectors were cultured to an optical density of 1.0 to 600 nm, and then resuspended in a solution containing 5% of sucrose, 10 mM of $MgCl_2$ and 0.005% of Silwet L-77 (# VIS-01; LEHLE SEEDS, Round Rock, Tex., USA). *A. thaliana* plants were infiltrated, under vacuum, with an *Agrobacterium* suspension for 5 minutes. The Ti seeds obtained from these plants infiltrated under vacuum were vernalized, sterilized and plated out onto an MS medium. The plants obtained were then transferred into earth and grown under standard conditions (20° C., 16 illuminations per day) in an incubator. The T2 seeds obtained from these plants were recovered for analysis (B. Kost et al., The Plant Journal, 1998, No. 16, pp. 393–401).

3. Overexpression of the APR in the Transformed Plants:

The APR activity was measured in the transformed plants above, in comparison with control plants, according to the method described in Kopriva et. al., 1999.

The plant material (maize calluses and *Arabidopsis* leaves) was extracted in a 50 mM of $NaKPO_4$ buffer (pH 8) supplemented with 30 mM $Na_2SO_3$, 0.5 mM 5'-AMP and 10 mM DTE (Imhof, 1994), using a glass homogenizer. The APR activity was measured in the extracts, using [$^{35}S$] sulfite production, evaluated as the volatile acid radioactivity formed in the presence of [$^{35}S$] APS and DTE (Brunold and Suter, 1990). The protein concentrations in the extracts were determined according to the Bradford method (1976), with bovine serum albumin as the standard.

Figure 5:
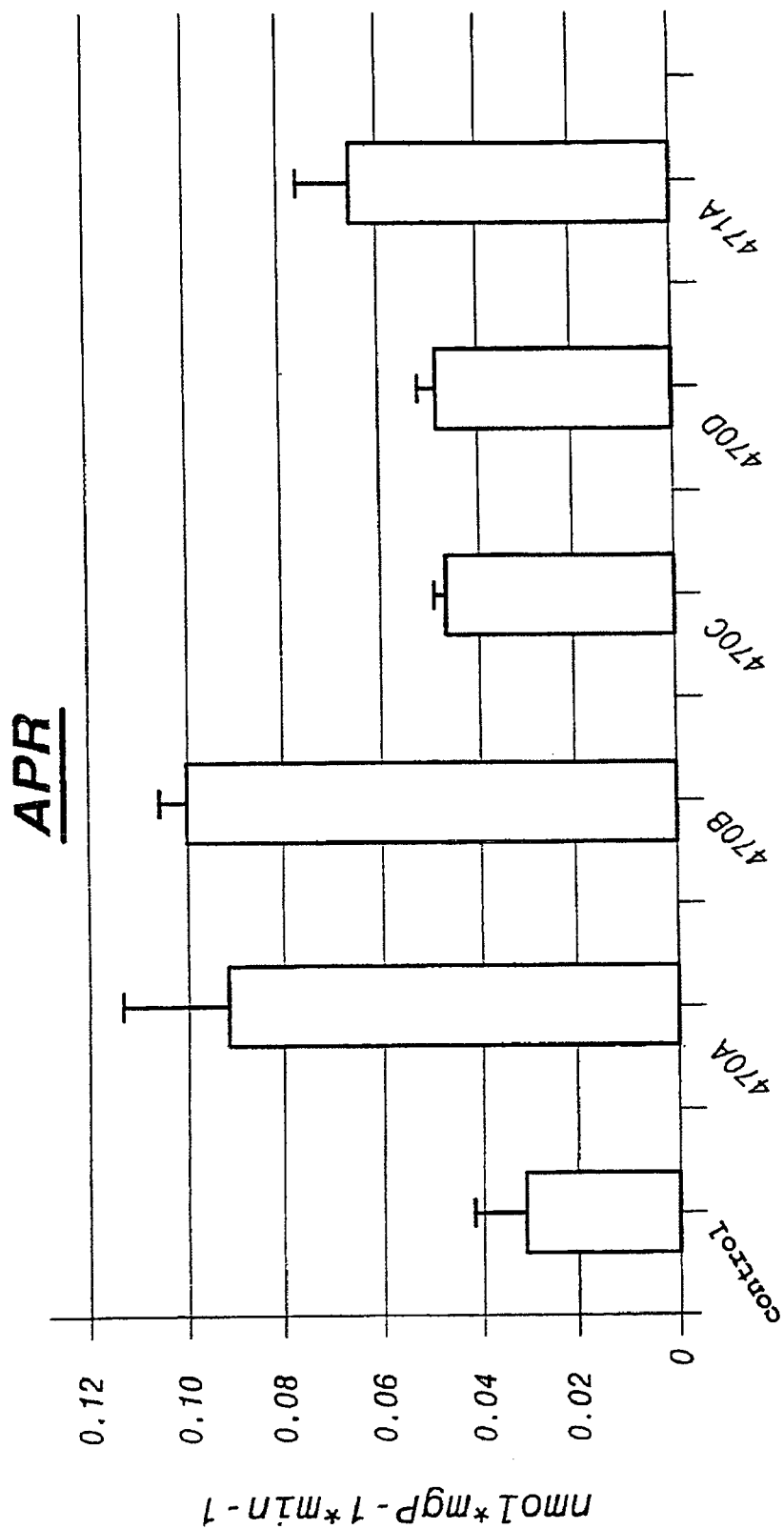
FIG. 5 is a graph showing the measurement of APR activity on maize calluses transformed with the construct actin promoter-intron~APR.
Figure 6:
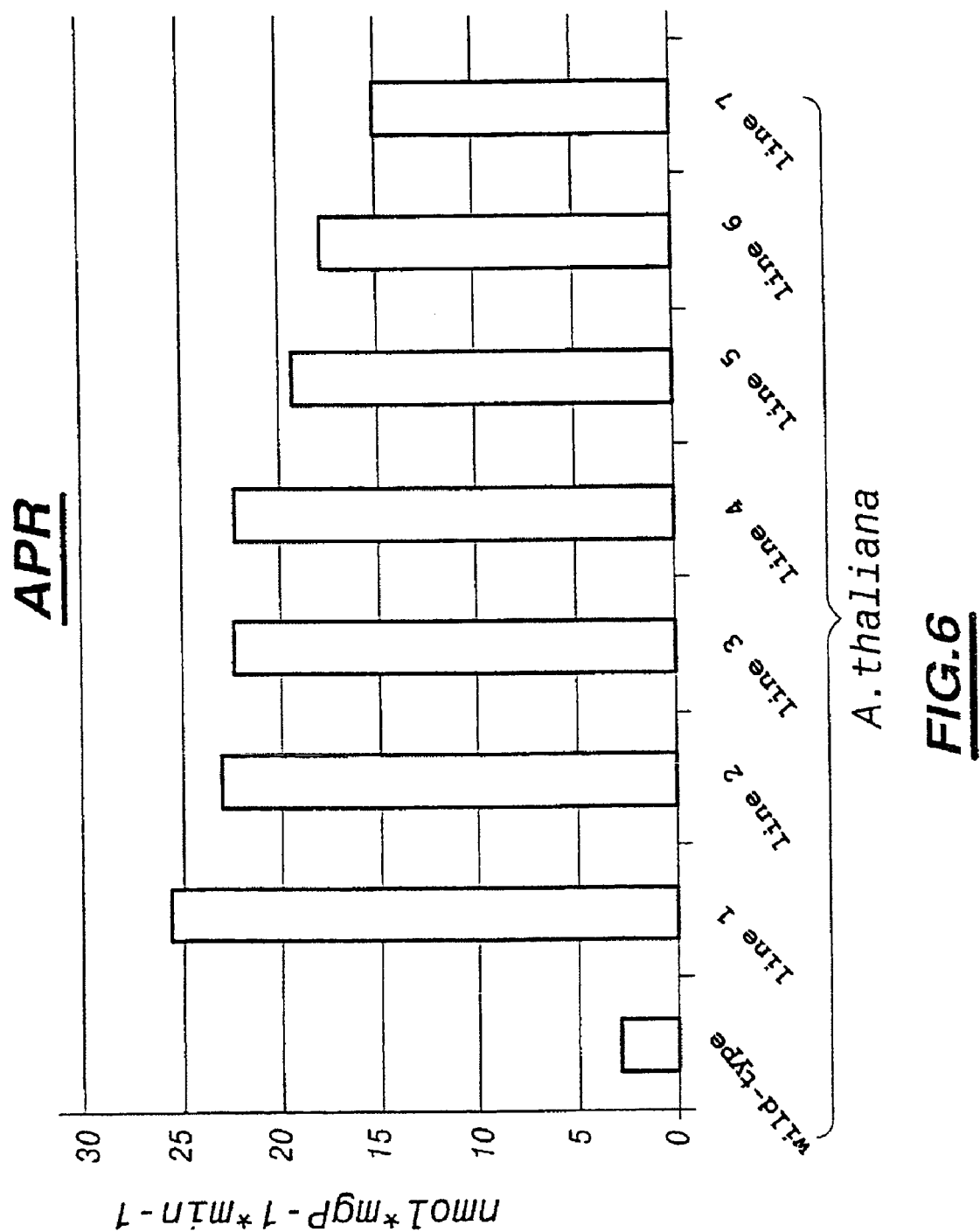
FIG. 6 is a graph showing the measurement of APR activity on leaves of transformed *Arabidopsis* plants (pro35S~APR).

As shown in FIGS. 5 and 6, the transformed plants (maize and *Arabidopsis*, respectively) exhibit an overexpression of APR enzyme.

Example 3

Production of Plants Enriched in Cysteine and Glutathione

Method:

The cysteine and glutathione contents of various organs of *Arabidopsis* transformed in example 2.2 and of maize transformed in example 2.1 were measured by the method of Ruegsegger et al., 1992, after reaction with monobromobimane. This method may be summarized as follows:

The thiols are separated and quantified by reverse-phase HPLC after reduction with $NaBH_4$ and reaction with monobromobimane which binds to the thiols and sends a fluorescent signal. The extracts are centrifuged for 30 minutes at 30 000 g and at 4° C. 600 µl of 0.2 M CHES (pH 9.3) and 100 µl of 40 mM $NaBH_4$ solution, freshly prepared, were added to 400 µl of supernatant. The negative control was an extraction medium. The mixture was maintained in ice for 30 minutes. For the reaction, 300 µl of this mixture were added to 15 µl of 15 mM monobromobimane dissolved in acetonitrile and maintained in the dark at ambient temperature for 15 minutes. The reaction was stopped by adding 250 µl of 5% (volume/volume) acetic acid. The samples were centrifuged for 10 minutes at 16 000 g and 4° C. and the undiluted supernatant was used to measure cysteine. A 20-fold dilution with 2.5% (volume/volume) acetic acid was used to measure glutathione GSH. The samples were then analyzed according to the method of Schupp and Rennenberg, 1988, on an HPLC Gold system (Beckman) with a Nucleosil 100-S $C_{18}$ column (4.0×250 mm; Machereu-Nagel, Oepsingen, Switzerland) and an SFM 25 fluorescence detector (Kontron, Zurich, Switzerland).

Figure 7:
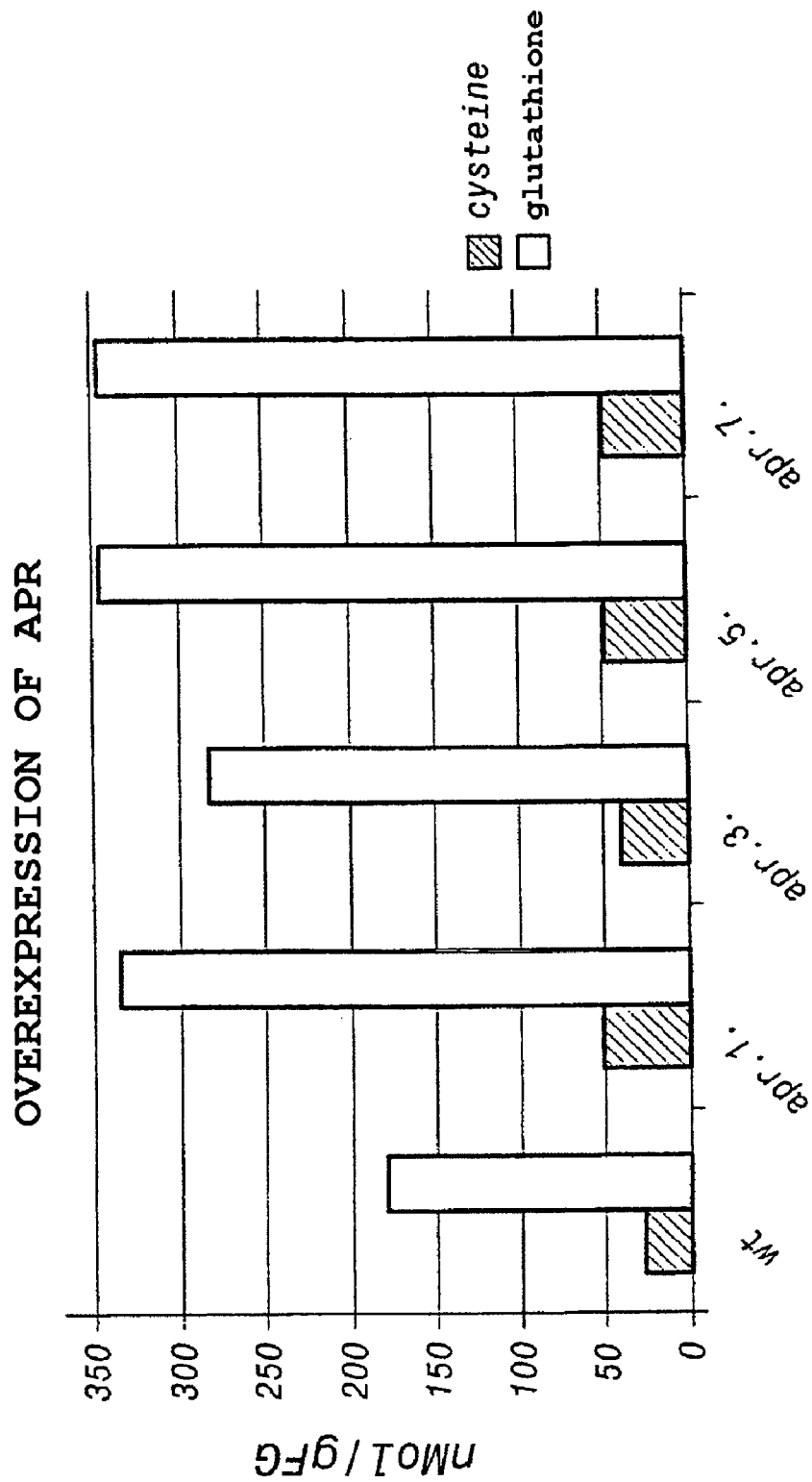
FIG. 7 is a graph plotting the measurements of the cysteine and glutathione contents from leaves of *A. thaliana* plants overexpressing the APR (construct pro35S~APR).

The results of the measurements of the cysteine and glutathione contents from leaves of *A. thaliana* overexpressing the APR are expressed in FIG. 7.

A significant increase in these cysteine and glutathione contents is observed compared with the nontransformed wild-type plant.

Figure 8A:
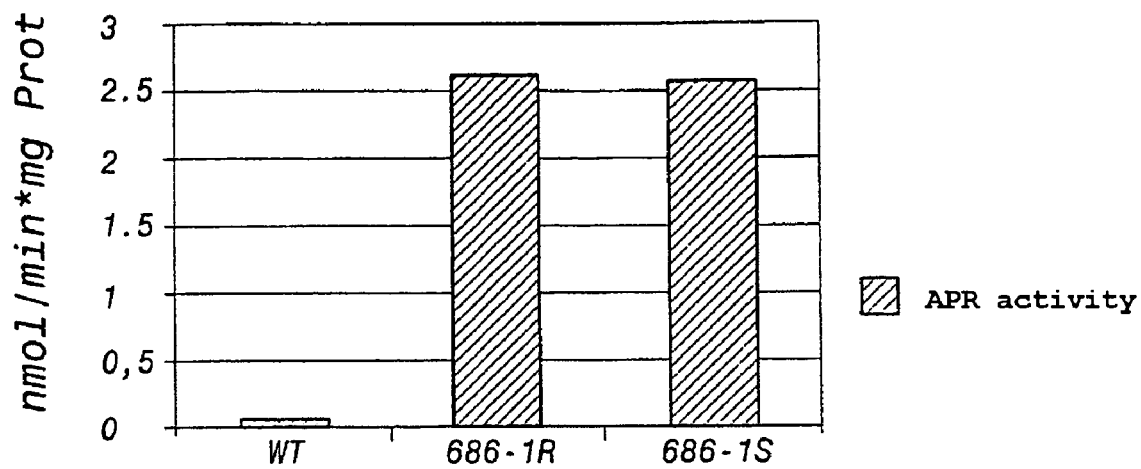
FIG. 8A is a graph plotting the measurement of APR activity on maize calluses transformed with the construct actin promoter-intron~APR.
Figure 8B:
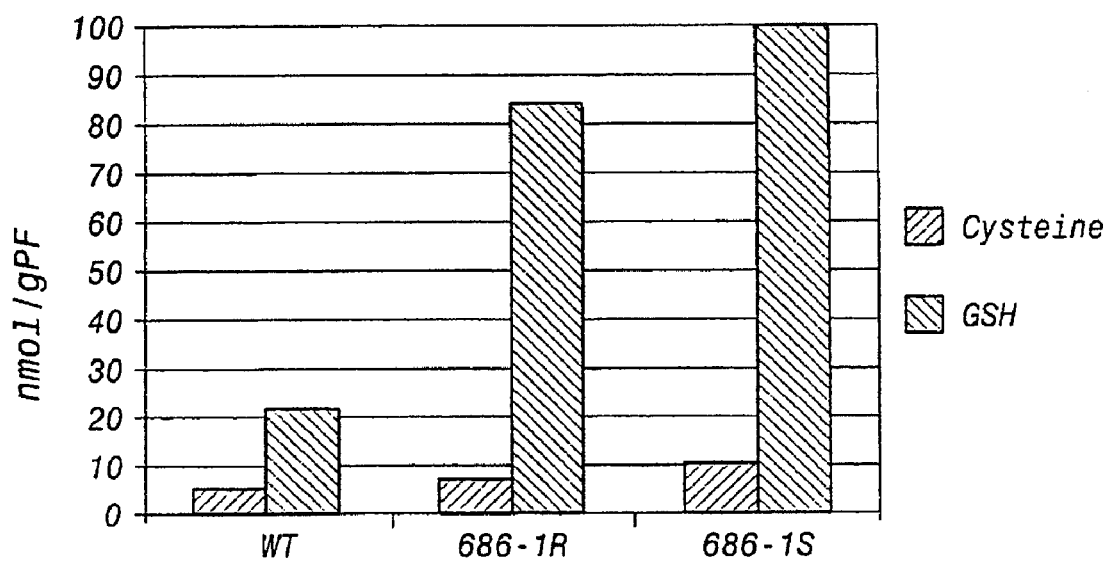
FIG. 8B is a graph plotting the measurements of the cysteine and glutathione contents from maize calluses overexpressing the APR.

The cysteine and glutathione contents of transformed and nontransformed maize calluses were also measured according to the same protocol. The results are expressed in FIGS. 8A and 8B. A significant increase in these cysteine and glutathione contents compared with the nontransformed calluses, correlated with the overexpression of the APR, is observed.

Measurements were also carried out on the plantlets obtained from these transformed calluses, and gave positive results.

REFERENCES

An et al., 1986, Plant Physiol., 81: 86–91
Armstrong (1994), *Maize Handbook*; M. Freeling, V. Walbot, Eds; 665–671
Bechtold et al., 1993, C. R. Acad. Sci. Paris, Life sciences, 316: 1194–1199
Bick and Leustek, 1998, Current opinion in Plant Biology, 1: 240–244
Bradford 1976, Anal. Biochem, 72: 248–254
Brunold et al., 1997, Prog. Bot., 58: 164–186
Brunold and Suter, 1990, Adenosine 5'-phosphosulfate sulfotransferase, I, P. Lea, Ed., Methods in Plant biochemistry vol. 3, Academic Press, London 339–343
Carrington et al., 1991, The plant cell, 3, 953–962
Carrington and Freed, 1990, Journal Virol., 64, 1590–1597
Chupeau et al., 1989, Biotechnology, 7 (5): 503–508
Dale et al., 1990, Gene, 91: 79–85
Depicker et al., 1982, Mol. Appl. Genet., 1: 561–573
J. Finer, (1992), *Plant Cell Report*, 11: 323–328
M. Fromm et al., 1990, Biotechnology, 8: 833–839
Guerche et al., (1987), *Mol. Gen. Genet.*, 206: 382
Guerineau et al., (1990), Plant. Mol. Biol., 15: 127–136
Gutierrez-Marcol et al., 1996, PNAS, vol. 93, pp. 13377–13382
Hartley et al., (1988), J. Mol. Biol., 202, 913–915
Heiss et al., 1999, Plant Mol. Biol., 39: 847–857
Herrera-Estrella et al., 1983, EMBO J. 2, 987–995
Imhof, 1994, Diploma work, Institute for Plant Physiology of the University of Berne
Ishida et al., (1996), *Nature Biotechnology*, 14: 745–750
Kay et al., 1987, Science, 236: 1299–1302
Klein, (1987), *Nature,* 327: 70–73
Koncz and Schell, 1986, Mol. Gen. Genet., 204, 383–396
Kopriva et al., 1999, The Plant Journal, 20 (1), 37–44
B. Kost et al., The Plant Journal, 1998, No. 16, pp. 393–401
May et al., 1998, Journal of Exp. Bot., 49: 649–667
McElroy et al., 1991, Mol. Gen. Genet., 231: 150–160
Murillo et al., 1995, Arch. Biochem. Biophys., 323: 195–204
Neuhaus et al., 1987, Theoretical and Applied Genetics, 75 (1): 30–36
Rennenberg et al., 1990, SPB Academic Publishing, The Hague, The Netherlands, pp. 53–65
Rennenberg et al., 1994, Prog. Bot., 55: 144–156
Robert et al., 1989, Plant Cell, 1: 569–578
Rogers et al., 1987, Methods in enzymology, 153, 253–277
Rüegsegger et al., 1992, Plant Physiol. No. 99, pp. 428–433
Saito et al., 1995, J. Biol. Chem., 270: 16321–6
J. Sambrook et al., Molecular cloning, A laboratory manual, Second edition, Cold Spring Harbor Laboratory Press, 1989
Schmidt et al., 1992, Annu. Rev. Plant Physiol. Plant Mol. Biol., 43: 325–349
Schocher et al., 1986, Biotechnology, 4: 1093–1096
Schupp and Rennenberg, 1988, Plant Sci., 57: 113–117
Vain et al., 1989, Plant Cell Tissue and organ culture, 18: 143–151
F. A. van Engelen et al., 1995, Transgenic Research, 4, 288–290
Watson et al., 1994, ADN recombinant [Recombinant DNA], Pub. De Boeck University, 273–292

The invention claimed is:

1. A method for obtaining a plant exhibiting an enriched cysteine and/or glutathione content, comprising the steps of:
    transforming at least one plant cell with a vector containing an expression cassette comprising a nucleic acid encoding an adenosine 5'-phosphosulfate reductase (APR) from *Lemna minor*;
    culturing the cell thus transformed so as to generate a plant containing said expression cassette in its genome thereby obtaining a plant exhibiting an enriched cysteine and/or glutathione content.

2. The method according to claim 1, wherein the plant cell is also transformed with a nucleic acid encoding a serine acetyltransferase (SAT).

3. The method according to claim 1, wherein said nucleic acid encoding the APR is SEQ ID NO: 1.

4. The method according to claim 1, wherein the expression cassette comprises a promoter which allows expression of the nucleic acid encoding the APR in seeds of the plant obtained.

5. The method according to claim 4, wherein the promoter is the HMWG promoter.

6. A plant or part of a plant exhibiting an enriched cysteine and/or glutathione content said plant or part of a plant comprising in its genome an expression cassette comprising a nucleic acid encoding an adenosine 5'-phosphosulfate reductase (APR) from *Lemna minor*.

7. The plant according to claim 6 which is maize.

8. The plant or part of a plant according to claim 1, wherein the nucleic acid encoding the APR is SEQ ID NO: 1.

9. The part of a plant according to claim 6, wherein said part of a plant is selected from the group consisting of seed, grain, fruit, leaf and tuber.

10. A hybrid transgenic plant which can be obtained by crossing at least one plant as defined in claim 6 with another plant which does not contain an expression cassette comprising a nucleic acid encoding an adenosine 5'-phosphosulfate reductase (APR) from *Lemna minor*.

11. A product containing the plant or part of the plant as defined in claim 6.

12. The product according to claim 11 which is a food product.

13. The product according to claim 12 which is a product for animal feeding.

14. A nucleic acid comprising the SEQ ID NO: 1 which encodes a *Lemna minor* APR enzyme.

15. An expression cassette comprising SEQ ID NO: 1 which encodes a *Lemna minor* APR enzyme.

16. The expression cassette of claim 15, wherein SEQ ID NO: 1 is functionally linked to the HMWG promoter.

17. An expression vector into which the expression cassette as claimed in claim 15 is inserted.

18. A host cell transformed with the vector as claimed in claim 17.

* * * * *

SEQUENCE LISTING

<160> NUMBER OF SEQ ID NOS: 11

<210> SEQ ID NO 1
<211> LENGTH: 1380
<212> TYPE: DNA

<213> ORGANISM: Lemna minor
<220> FEATURE:
<221> NAME/KEY: CDS
<222> LOCATION: (1)..(1377)

<400> SEQUENCE: 1

| | | | | | | | | | | | | | | | | |
|---|---|---|---|---|---|---|---|---|---|---|---|---|---|---|---|---|
| atg | tcg | gcc | gca | gca | gca | act | atg | gcg | ggc | tcg | ctc | tct | tca | cac | acg | 48 |
| Met | Ser | Ala | Ala | Ala | Ala | Thr | Met | Ala | Gly | Ser | Leu | Ser | Ser | His | Thr | |
| 1 | | | | 5 | | | | | 10 | | | | | 15 | | |
| ctc | tcc | tcc | cgc | gaa | ttt | tca | gga | gga | ttg | cag | gtc | agc | tct | acg | agg | 96 |
| Leu | Ser | Ser | Arg | Glu | Phe | Ser | Gly | Gly | Leu | Gln | Val | Ser | Ser | Thr | Arg | |
| | | | 20 | | | | | 25 | | | | | 30 | | | |
| gtg | agg | aaa | ttg | cag | agg | gga | gcg | ttt | gct | ccg | atg | cgg | cct | ctg | tgt | 144 |
| Val | Arg | Lys | Leu | Gln | Arg | Gly | Ala | Phe | Ala | Pro | Met | Arg | Pro | Leu | Cys | |
| | | 35 | | | | | 40 | | | | | 45 | | | | |
| gcg | gtg | gat | cca | ggg | agg | aag | agc | cag | tcg | cca | gtg | gcg | ccg | ctg | gcc | 192 |
| Ala | Val | Asp | Pro | Gly | Arg | Lys | Ser | Gln | Ser | Pro | Val | Ala | Pro | Leu | Ala | |
| | 50 | | | | | 55 | | | | | 60 | | | | | |
| gcc | gtg | ccg | tcg | tcc | acc | tct | gat | gcc | gtg | act | ctt | gtc | caa | gca | gca | 240 |
| Ala | Val | Pro | Ser | Ser | Thr | Ser | Asp | Ala | Val | Thr | Leu | Val | Gln | Ala | Ala | |
| 65 | | | | | 70 | | | | | 75 | | | | | 80 | |
| gaa | acg | agc | acc | gtt | gac | gtg | gtt | gat | ttt | gag | aag | ctc | gcg | agc | gag | 288 |
| Glu | Thr | Ser | Thr | Val | Asp | Val | Val | Asp | Phe | Glu | Lys | Leu | Ala | Ser | Glu | |
| | | | | 85 | | | | | 90 | | | | | 95 | | |
| cta | gag | cgc | gca | tcg | cct | ctc | gag | att | atg | gac | aag | gct | ctg | gag | atg | 336 |
| Leu | Glu | Arg | Ala | Ser | Pro | Leu | Glu | Ile | Met | Asp | Lys | Ala | Leu | Glu | Met | |
| | | | 100 | | | | | 105 | | | | | 110 | | | |
| ttc | ggt | aac | gat | att | gcc | atc | gcc | ttc | agc | ggg | gcg | gag | gac | gtt | gct | 384 |
| Phe | Gly | Asn | Asp | Ile | Ala | Ile | Ala | Phe | Ser | Gly | Ala | Glu | Asp | Val | Ala | |
| | | | 115 | | | | | 120 | | | | | 125 | | | |
| ctg | atc | gag | tac | gca | cgc | cta | acc | gga | cga | cct | ttc | agg | gtg | ttc | agt | 432 |
| Leu | Ile | Glu | Tyr | Ala | Arg | Leu | Thr | Gly | Arg | Pro | Phe | Arg | Val | Phe | Ser | |
| | 130 | | | | | 135 | | | | | 140 | | | | | |
| ctc | gac | acc | ggc | agg | cta | aac | cca | gag | aca | tac | cga | ttc | ttc | gat | gaa | 480 |
| Leu | Asp | Thr | Gly | Arg | Leu | Asn | Pro | Glu | Thr | Tyr | Arg | Phe | Phe | Asp | Glu | |
| 145 | | | | | 150 | | | | | 155 | | | | | 160 | |
| gta | gag | aag | cgc | tac | aac | atc | cgc | atc | gag | tac | atg | ttc | ccc | gac | gcg | 528 |
| Val | Glu | Lys | Arg | Tyr | Asn | Ile | Arg | Ile | Glu | Tyr | Met | Phe | Pro | Asp | Ala | |
| | | | | 165 | | | | | 170 | | | | | 175 | | |
| gtg | gaa | gtc | caa | gcc | ctc | gtg | cga | agc | aaa | ggc | ctc | ttt | tcc | ttc | tac | 576 |
| Val | Glu | Val | Gln | Ala | Leu | Val | Arg | Ser | Lys | Gly | Leu | Phe | Ser | Phe | Tyr | |
| | | | 180 | | | | | 185 | | | | | 190 | | | |
| gag | gac | ggg | cac | cag | gag | tgc | tgc | aga | gtg | aga | aag | gtg | agg | ccc | ctt | 624 |
| Glu | Asp | Gly | His | Gln | Glu | Cys | Cys | Arg | Val | Arg | Lys | Val | Arg | Pro | Leu | |
| | | | 195 | | | | | 200 | | | | | 205 | | | |
| aga | aga | gct | ctc | aga | ggc | ctc | aga | gcc | tgg | atc | acc | ggc | cag | cgc | aag | 672 |
| Arg | Arg | Ala | Leu | Arg | Gly | Leu | Arg | Ala | Trp | Ile | Thr | Gly | Gln | Arg | Lys | |
| | 210 | | | | | 215 | | | | | 220 | | | | | |
| gac | cag | tct | ccc | ggc | acc | cga | gcc | agc | gtt | ccc | acc | gtc | cag | gtg | gat | 720 |
| Asp | Gln | Ser | Pro | Gly | Thr | Arg | Ala | Ser | Val | Pro | Thr | Val | Gln | Val | Asp | |
| 225 | | | | | 230 | | | | | 235 | | | | | 240 | |
| cct | tcg | ttc | gag | gga | ttt | gaa | ggc | gga | aca | ggc | agc | tta | atc | aaa | tgg | 768 |
| Pro | Ser | Phe | Glu | Gly | Phe | Glu | Gly | Gly | Thr | Gly | Ser | Leu | Ile | Lys | Trp | |
| | | | | 245 | | | | | 250 | | | | | 255 | | |
| aac | ccc | gtg | gcg | aac | gta | gac | ggg | cag | gat | atc | tgg | aga | ttc | ctg | aga | 816 |
| Asn | Pro | Val | Ala | Asn | Val | Asp | Gly | Gln | Asp | Ile | Trp | Arg | Phe | Leu | Arg | |
| | | | 260 | | | | | 265 | | | | | 270 | | | |
| acg | atg | gcc | gtt | cca | gtg | aac | tcc | ctc | cac | tcc | caa | ggg | tac | gtg | tca | 864 |
| Thr | Met | Ala | Val | Pro | Val | Asn | Ser | Leu | His | Ser | Gln | Gly | Tyr | Val | Ser | |
| | | 275 | | | | | 280 | | | | | 285 | | | | |

-continued

| | | | | | | | | | | | | | | | |
|---|---|---|---|---|---|---|---|---|---|---|---|---|---|---|---|
| atc | ggc | tgc | gag | cca | tgc | acg | cgg | ccg | gtc | cta | cca | gga | cag | cac | gag | 912
| Ile | Gly | Cys | Glu | Pro | Cys | Thr | Arg | Pro | Val | Leu | Pro | Gly | Gln | His | Glu |
| | 290 | | | | 295 | | | | 300 | | | | | | |
| agg | gaa | gga | agg | tgg | tgg | tgg | gag | gac | gcg | aaa | gcc | aag | gaa | tgc | ggg | 960
| Arg | Glu | Gly | Arg | Trp | Trp | Trp | Glu | Asp | Ala | Lys | Ala | Lys | Glu | Cys | Gly |
| 305 | | | | | 310 | | | | | 315 | | | | | 320 |
| ctc | cac | aag | ggc | aac | atc | aag | caa | gac | gag | tcc | gtg | cct | ccc | tcc | agc | 1008
| Leu | His | Lys | Gly | Asn | Ile | Lys | Gln | Asp | Glu | Ser | Val | Pro | Pro | Ser | Ser |
| | | | | 325 | | | | | 330 | | | | | 335 | |
| aac | ggc | aac | ggc | acc | gcg | ccg | tcg | gat | ctc | ttc | tcc | gtc | gtt | tct | ctg | 1056
| Asn | Gly | Asn | Gly | Thr | Ala | Pro | Ser | Asp | Leu | Phe | Ser | Val | Val | Ser | Leu |
| | | | 340 | | | | | 345 | | | | | 350 | | |
| agc | cgg | cca | ggc | atg | gag | aac | ttg | ctc | cgc | ctg | gag | agc | cgg | aag | gac | 1104
| Ser | Arg | Pro | Gly | Met | Glu | Asn | Leu | Leu | Arg | Leu | Glu | Ser | Arg | Lys | Asp |
| | | 355 | | | | | 360 | | | | | 365 | | | |
| tcg | tgg | ctt | gtc | gtg | ctc | tat | gct | ccc | tgg | tgc | cgc | ttc | tgc | cag | ggg | 1152
| Ser | Trp | Leu | Val | Val | Leu | Tyr | Ala | Pro | Trp | Cys | Arg | Phe | Cys | Gln | Gly |
| | 370 | | | | 375 | | | | | 380 | | | | | |
| atg | gag | gag | tcg | ttc | aac | gag | gtg | gca | gga | gta | ctc | ggc | ggc | gac | tca | 1200
| Met | Glu | Glu | Ser | Phe | Asn | Glu | Val | Ala | Gly | Val | Leu | Gly | Gly | Asp | Ser |
| 385 | | | | | 390 | | | | | 395 | | | | | 400 |
| gga | gtg | aag | gtg | ggc | aaa | ttc | aga | gcc | gac | gga | gac | gcg | aga | gct | ttc | 1248
| Gly | Val | Lys | Val | Gly | Lys | Phe | Arg | Ala | Asp | Gly | Asp | Ala | Arg | Ala | Phe |
| | | | | 405 | | | | | 410 | | | | | 415 | |
| gcg | gag | gag | atc | ggg | ctg | gtg | agt | ttt | ccc | acc | ata | ctc | ttc | ttc | ccg | 1296
| Ala | Glu | Glu | Ile | Gly | Leu | Val | Ser | Phe | Pro | Thr | Ile | Leu | Phe | Phe | Pro |
| | | | 420 | | | | | 425 | | | | | 430 | | |
| aag | cac | gcg | tcg | aaa | ccg | gtc | aag | tac | ccg | tcg | gag | cag | aga | gac | gtc | 1344
| Lys | His | Ala | Ser | Lys | Pro | Val | Lys | Tyr | Pro | Ser | Glu | Gln | Arg | Asp | Val |
| | | 435 | | | | | 440 | | | | | 445 | | | |
| gac | tct | ctg | ctc | gcc | ttc | gtc | aac | gcc | ctt | cgc | tga | | | | | 1380
| Asp | Ser | Leu | Leu | Ala | Phe | Val | Asn | Ala | Leu | Arg | | | | | |
| | 450 | | | | 455 | | | | | | | | | | |

<210> SEQ ID NO 2
<211> LENGTH: 459
<212> TYPE: PRT
<213> ORGANISM: Lemna minor

<400> SEQUENCE: 2

Met Ser Ala Ala Ala Thr Met Ala Gly Ser Leu Ser Ser His Thr
1               5                   10                  15

Leu Ser Ser Arg Glu Phe Ser Gly Gly Leu Gln Val Ser Ser Thr Arg
            20                  25                  30

Val Arg Lys Leu Gln Arg Gly Ala Phe Ala Pro Met Arg Pro Leu Cys
        35                  40                  45

Ala Val Asp Pro Gly Arg Lys Ser Gln Ser Pro Val Ala Pro Leu Ala
    50                  55                  60

Ala Val Pro Ser Ser Thr Ser Asp Ala Val Thr Leu Val Gln Ala Ala
65                  70                  75                  80

Glu Thr Ser Thr Val Asp Val Val Asp Phe Glu Lys Leu Ala Ser Glu
                85                  90                  95

Leu Glu Arg Ala Ser Pro Leu Glu Ile Met Asp Lys Ala Leu Glu Met
            100                 105                 110

Phe Gly Asn Asp Ile Ala Ile Ala Phe Ser Gly Ala Glu Asp Val Ala
        115                 120                 125

Leu Ile Glu Tyr Ala Arg Leu Thr Gly Arg Pro Phe Arg Val Phe Ser
    130                 135                 140

```
Leu Asp Thr Gly Arg Leu Asn Pro Glu Thr Tyr Arg Phe Phe Asp Glu
145                 150                 155                 160

Val Glu Lys Arg Tyr Asn Ile Arg Ile Glu Tyr Met Phe Pro Asp Ala
                165                 170                 175

Val Glu Val Gln Ala Leu Val Arg Ser Lys Gly Leu Phe Ser Phe Tyr
            180                 185                 190

Glu Asp Gly His Gln Glu Cys Cys Arg Val Arg Lys Val Arg Pro Leu
        195                 200                 205

Arg Arg Ala Leu Arg Gly Leu Arg Ala Trp Ile Thr Gly Gln Arg Lys
    210                 215                 220

Asp Gln Ser Pro Gly Thr Arg Ala Ser Val Pro Thr Val Gln Val Asp
225                 230                 235                 240

Pro Ser Phe Glu Gly Phe Glu Gly Gly Thr Gly Ser Leu Ile Lys Trp
                245                 250                 255

Asn Pro Val Ala Asn Val Asp Gly Gln Asp Ile Trp Arg Phe Leu Arg
            260                 265                 270

Thr Met Ala Val Pro Val Asn Ser Leu His Ser Gln Gly Tyr Val Ser
        275                 280                 285

Ile Gly Cys Glu Pro Cys Thr Arg Pro Val Leu Pro Gly Gln His Glu
    290                 295                 300

Arg Glu Gly Arg Trp Trp Trp Glu Asp Ala Lys Ala Lys Glu Cys Gly
305                 310                 315                 320

Leu His Lys Gly Asn Ile Lys Gln Asp Glu Ser Val Pro Pro Ser Ser
                325                 330                 335

Asn Gly Asn Gly Thr Ala Pro Ser Asp Leu Phe Ser Val Val Ser Leu
            340                 345                 350

Ser Arg Pro Gly Met Glu Asn Leu Leu Arg Leu Glu Ser Arg Lys Asp
        355                 360                 365

Ser Trp Leu Val Val Leu Tyr Ala Pro Trp Cys Arg Phe Cys Gln Gly
    370                 375                 380

Met Glu Glu Ser Phe Asn Glu Val Ala Gly Val Leu Gly Gly Asp Ser
385                 390                 395                 400

Gly Val Lys Val Gly Lys Phe Arg Ala Asp Gly Asp Ala Arg Ala Phe
                405                 410                 415

Ala Glu Glu Ile Gly Leu Val Ser Phe Pro Thr Ile Leu Phe Phe Pro
            420                 425                 430

Lys His Ala Ser Lys Pro Val Lys Tyr Pro Ser Glu Gln Arg Asp Val
        435                 440                 445

Asp Ser Leu Leu Ala Phe Val Asn Ala Leu Arg
450                 455

<210> SEQ ID NO 3
<211> LENGTH: 20
<212> TYPE: DNA
<213> ORGANISM: Lemna minor

<400> SEQUENCE: 3
actggtcctt gcgctggccg                                                 20

<210> SEQ ID NO 4
<211> LENGTH: 38
<212> TYPE: DNA
<213> ORGANISM: Lemna minor

<400> SEQUENCE: 4
gaccacgcgt atcgatgtcg actttttttt tttttttt                             38
```

```
<210> SEQ ID NO 5
<211> LENGTH: 22
<212> TYPE: DNA
<213> ORGANISM: Lemna minor

<400> SEQUENCE: 5
gtcgacatcg atacgcgtgg tc                                              22

<210> SEQ ID NO 6
<211> LENGTH: 20
<212> TYPE: DNA
<213> ORGANISM: Lemna minor

<400> SEQUENCE: 6
gtgatccagg ctctgaggcc                                                 20

<210> SEQ ID NO 7
<211> LENGTH: 22
<212> TYPE: DNA
<213> ORGANISM: Lemna minor

<400> SEQUENCE: 7
tctgagagct cttctaaggg gc                                              22

<210> SEQ ID NO 8
<211> LENGTH: 20
<212> TYPE: DNA
<213> ORGANISM: Lemna minor

<400> SEQUENCE: 8
accaggacag cacgagaggg                                                 20

<210> SEQ ID NO 9
<211> LENGTH: 20
<212> TYPE: DNA
<213> ORGANISM: Lemna minor

<400> SEQUENCE: 9
aaggtggtgg tgggaggacg                                                 20

<210> SEQ ID NO 10
<211> LENGTH: 39
<212> TYPE: DNA
<213> ORGANISM: Lemna minor

<400> SEQUENCE: 10
cgtctagagg ccatggcggc cgcagcagca actatggcg                            39

<210> SEQ ID NO 11
<211> LENGTH: 34
<212> TYPE: DNA
<213> ORGANISM: Lemna minor

<400> SEQUENCE: 11
aaagaattcc actctagaag cgaagagaag aggc                                 34
```